United States Patent
Verzal et al.

(10) Patent No.: US 9,682,226 B2
(45) Date of Patent: Jun. 20, 2017

(54) ELECTRONIC LEAD CONNECTION AND RELATED DEVICES

(71) Applicant: Envoy Medical Corporation, St. Paul, MN (US)

(72) Inventors: Kevin E. Verzal, Lino Lakes, MN (US); Benjamin R. Whittington, Roseville, MN (US)

(73) Assignee: ENVOY MEDICAL CORPORATION, St. Paul, MN (US)

( * ) Notice: Subject to any disclaimer, the term of this patent is extended or adjusted under 35 U.S.C. 154(b) by 0 days.

(21) Appl. No.: 14/099,369

(22) Filed: Dec. 6, 2013

(65) Prior Publication Data
US 2015/0157853 A1   Jun. 11, 2015

(51) Int. Cl.
*A61N 1/05* (2006.01)
*H01R 13/52* (2006.01)
*A61N 1/375* (2006.01)
*H01R 24/58* (2011.01)

(52) U.S. Cl.
CPC .......... *A61N 1/0551* (2013.01); *A61N 1/056* (2013.01); *A61N 1/3752* (2013.01); *H01R 13/5219* (2013.01); *H01R 24/58* (2013.01); *H01R 2201/12* (2013.01); *Y10T 29/49117* (2015.01)

(58) Field of Classification Search
CPC .......................... A61N 1/3752; A61N 1/3754
USPC ....................................... 607/37–38
See application file for complete search history.

(56) References Cited

U.S. PATENT DOCUMENTS

| | | | |
|---|---|---|---|
| 6,039,685 | A | 3/2000 | Bushek |
| 6,755,778 | B2 | 6/2004 | Kroll et al. |
| 7,297,101 | B2 | 11/2007 | Neisz et al. |
| 7,305,267 | B2 | 12/2007 | Hector |

*Primary Examiner* — Paula J Stice
(74) *Attorney, Agent, or Firm* — Kagan Binder, PLLC

(57) ABSTRACT

Described are lead connections for electrically connecting a lead terminal and a lead channel; the lead connection can be useful in an electronic device such as an implantable electronic device, such as a hearing implant.

22 Claims, 8 Drawing Sheets

ELECTRONIC LEAD CONNECTION AND RELATED DEVICES

FIELD OF THE INVENTION

The invention relates to implantable electronic devices that include a lead channel, wherein the lead channel includes a vent to equalize pressure during insertion of a lead terminal into the lead channel.

BACKGROUND

In medical technologies, innovative implantable electronic devices have become relatively common, yet provide invaluable improvement to the lives of patients. These devices can perform, improve, or control anatomical functions ranging from hearing, pain suppression, appetite control, urinary continence, and cardiac rhythms, among others.

A requirement of an implantable device is that the device be well sealed to prevent bodily fluid from passing into the device interior after implantation, which would allow the fluid to interfere with electrical functioning of the device. Sealing an implantable device can be a relatively simple achievement, by itself. But implantable devices typically require one or more lead connections that are used to connect an electronic lead to an electronic processor. For ease of use and the ability to replace individual components of an implantable device, components of an implantable lead connection are separate pieces of an implantable device and are typically connected by a surgeon during a surgical procedure. The lead connection cannot be pre-sealed before implantation, but must instead be assembled during surgery in a manner that results in an impermeably sealed connection that is also mechanically secure and reliable. The need to connect the electrical lead components during surgery to produce a well-sealed connection creates certain challenges, because a surgeon should not be overly burdened with complicated tasks required to secure the sealed connection, during a surgical procedure.

A standard component of a sealed connection is a gasket. A known disadvantage of a sealing gasket is that a gasket can trap air inside of a connection and produce a pressurized interior. Air contained in a channel of a lead connection is held in the channel by the gasket and becomes compressed as the lead terminal is advanced within the channel. A first undesired effect of air becoming trapped by a gasket upon making a connection is an increased insertion force. A more serious effect can be pressurization of the air contained in the channel as the lead terminal is inserted. The pressurized lead channel can tend to push against the inserted lead terminal in a manner that may potentially cause the lead terminal to move within the channel after implantation, e.g., to be dislodged or pushed out of a fully-inserted position within the channel by being at least partially moved within or partially separated from the lead channel. As a practical matter the connection—due to the pressurized air within the lead channel—is less secure than necessary for an implanted device.

The implantable lead connection must be sealed to prevent leakage of fluid into the device and, preferably, to prevent any leaking of electrical current or signal between two or more electrical contacts within the implanted device, or between any one of multiple electrical contacts of an implanted device and the environment external to the implanted device and internal to the patient. Gaskets mounted between a lead terminal and a lead channel are typically used to create the seals between electrical contacts of a single lead connection, and also between the contacts of a lead connection and the patient anatomy.

Overall, the sealed implantable lead connection, with a lead terminal fully-inserted in a lead channel, must be both sealed and secure for an extended time in an environment of a patient anatomy with attendant bodily fluids. Secure means that the lead connection, once completed during a surgical procedure, is sufficiently secure to not subsequently fail within the patient, e.g., to not separate or decouple to any functional extent after surgical placement of the implant in a patient. As a practical matter, the connection must be sufficiently secure that the connection does not stand an unacceptably high risk of failing at any time following surgery. Sealed as a practical matter means that the connection does not fail, malfunction, or produce detrimental functionality due to leakage of fluid into the interior of the lead connection or the implanted device.

According to past and present designs, implantable lead connections have been used that avoid or overcome the problems resulting from a gasket seal and pressurized lead channel, using at least two different or complementary approaches. One approach has been to alleviate the increased pressure within the lead channel by venting the lead channel during or after fully inserting a lead terminal into a lead channel. A second approach has been to mechanically secure the lead terminal in place within the lead channel, after full insertion, using a mechanical device to produce a frictional force that prevents subsequent movement, i.e., a mechanical securing or locking device that produces a force that is sufficient to overcome the force of the pressurized lead channel interior and prevent any subsequent movement of the lead terminal (e.g., slight separation) after implantation, even if the internal pressure remains.

One example of a previous design is found in U.S. Pat. No. 7,305,267. That document shows an implantable connector that includes a "lead retention element" such as screw port or "set screw," which is also vented, extending through an opening in a sidewall of a connector module of an implantable lead connection. The set screw design performs a venting function because the threaded bore in which the set screw is seated will allow for passage of air from a lead channel to an exterior. The set screw also performs the function of a locking mechanism by placing a lateral holding force on the lead terminal within the channel.

Because a threaded bore opening that holds the set screw at the channel wall will necessarily allow for at least some amounts of fluid and electrical leakage, a seal in the form of a polymeric cover must be in place over the bore and the set screw before implantation. A typical vented set screw port has a silicone diaphragm or "self-sealing" membrane placed over the set screw. The diaphragm can include a small "slit" opening or may otherwise allow a screwdriver to pass through to allow the set screw to be turned and tightened, also allowing air to escape the channel during insertion. Upon removal of the screwdriver, the membrane in its natural state is considered to close and to produce a "seal" that is useful to prevent fluid flow and provide electrical isolation. In practice, however, these self-sealing membranes always include a small slot or opening through which at least a minor amount of fluid and electrical leakage can occur.

In use, this set-screw and self-sealing membrane are not adequate for all types of implantable electronic devices. The design may perform well for pacemaker devices, for example, which do not require relatively high levels of signal detector sensitivity, or high fidelity signal processing or delivery. But a vented set screw design and self-sealing membrane do not provide adequate electrical isolation for implants that do require highly sensitive and high fidelity signal processing, as do, for example, hearing implants. A "self-sealing" membrane does not completely seal. In a hearing implant, an eventual result of the imperfect seal is fluid and electrical leakage at the site of the set screw, allowing electrical leakage either between two electrical contacts of the implant or between an electrical contact and the patient environment. The amount of electrical leaking can result in electrical feedback between an input and an output of the electronic device, which can impact the performance of a hearing implant or other implantable device that requires a high sensitivity or high fidelity input or output signal.

Another example of a previous lead connection design that involves venting a lead channel is found in U.S. Pat. No. 6,039,685. This vented design includes a vent that is closed or covered by a "self-sealing resilient plug." During or after inserting a lead terminal into a lead channel, the channel is vented by passing a "non-coring" needle through the resilient plug. Like the "self-sealing" set screw design, this design also allows for potential leakage of fluid through the opening made in the resilient plug by the "non-coring" needle. Another disadvantage is that during surgical placement, this design requires a surgeon to perform the step of passing the non-coring needle through the plug to vent the channel.

Still another example of a vent design is a vent between an outer lead terminal surface and an internal lead channel wall, at a location of a sealing gasket during insertion of the lead terminal. Air can be vented from the lead channel during insertion by placing a small tubular structure (e.g., a polytetrafluoroethylene (PTFE) tube) inside of the channel at an inner channel wall, e.g., as a part of the manufacturing process. During surgery, when a lead terminal is inserted into the channel that contains the PTFE tube at an inner surface, the PTFE tube creates a gap at the gasket between the inner wall of the bore and the lead terminal. The gap in the gasket allows air to escape the gasket near the PTFE tube during insertion. After the lead terminal is fully inserted, the PTFE tube can be removed, causing the gasket to fully seal the lead channel from the exterior environment, providing electrical isolation and a fluid-tight seal. A shortcoming of this design is that it requires added steps for a surgeon.

Another potential shortcoming to the these previous lead connector designs is that in use they can lack consistency or reproducibility in venting a channel. For example, when using a PTFE tube to allow air to escape from a channel, a surgeon may not always be certain that the tube was correctly placed, or was effective to remove a necessary amount of air from the channel; but after placement of the lead in the channel and removal of the tube, in the event of doubt on the effectiveness of the vent, a surgeon would have great difficulty separating the lead from the channel and reconfiguring the tube to make a second attempt. If doubt were present as to the effectiveness of the tube to vent the channel, the surgeon would have little choice but to continue with the implantation procedure without knowing for certain that the channel does not contain potentially excessive pressure, or to scrap the unit and complete the surgery using a secondary device.

SUMMARY

In view of the above-described options for avoiding the problem of pressurizing a lead channel upon insertion of a lead terminal, electronics product designers would benefit from added improvement to lead connection designs. Preferred designs would provide a sealed and secure lead connection between a lead terminal and a lead channel without a complicated or multi-step method for preparing the connection; desirably, the connection could be prepared with a single step insertion of the lead terminal into the channel, meaning a surgeon could insert a lead terminal into a lead channel, confirm full insertion, and need not perform any additional step to vent the channel, mechanically secure the lead terminal within the lead channel, or remove or close a vent. By a single pushing step, to the exclusion of any added step by a surgeon to manipulate a vent or a mechanical locking or securing mechanism, the lead terminal can be fully inserted in the channel; with only the single pushing step the channel would be vented at least sufficiently to prevent an increase in internal channel pressure that would increase a risk of movement, separation, or partial de-coupling of the lead terminal relative to the lead channel, and the terminal would be securely held in its fully-inserted position.

The following description relates to implantable lead connections that are vented by a vent hole in a lead channel, the vent hole being located on a distal side of one or more sealing gasket of a lead terminal, while the lead terminal is situated in a fully-inserted position. A "fully-inserted position" refers to an engagement of the lead terminal with the lead channel wherein: a terminal contact is electrically engaged with a channel contact; a gasket located at an outer surface of the lead terminal engages an inner surface of the channel wall to produce a seal between the two surfaces; the gasket is located between an open end of the channel (the distal end) and a closed end (the forward end) of the channel; a channel vent hole is located between the gasket and the open end; and the terminal contact and channel contact are located between the gasket and the closed forward end. This arrangement of the gasket, vent opening, and contacts, allows the lead terminal to be partially inserted into the channel during an initial insertion and venting stage during which the gasket moves from the open end of the channel toward and up to the channel vent hole; during this initial insertion and venting stage, air pushed by the gasket escapes the channel through the vent. With additional insertion, after the gasket passes the location of the vent hole (along a length of the channel), air no longer escapes the channel through the vent and the channel is sealed, but the amount of air that has become trapped within the channel has been reduced by the venting that occurred during the initial insertion and venting stage. Preferably, the amount of air contained in the sealed channel is sufficiently low that the channel is not unduly pressurized; the pressure will be above ambient or atmospheric pressure but will not be at a level that creates an undue risk of de-coupling of the lead connection. Although this vent design does not completely vent all of the air out of the lead channel, and does result in an above-ambient pressure in the sealed channel, a major amount of air has been vented and the pressurization that is produced will still provide a relatively reduced insertion force (relative to an unvented connection) during insertion of the lead terminal into the lead channel, and a substantially reduced risk of the lead terminal moving relative to the channel, e.g., backing out of the channel, due to pressure within the sealed channel.

A vented channel can be part of an overall implantable lead connection design that may or many not include an additional securing or locking mechanism to further prevent the lead from backing out of the sealed channel due to pressure within the sealed channel. Devices and methods as described can optionally involve a mechanical securement mechanisms such as a set screw, detent, latch, threaded engagement, or the like. Certain embodiments can include a passive securement mechanism such as a frictional engagement that does not require manipulation, e.g., a detent such as a ball detent, an automatic latch, or an arrangement of an annular spring and corresponding grooves or surfaces of the terminal and channel. Other implant devices and methods as described can exclude the need for or the presence of any such active (e.g., requires manipulation by a user, such as a set screw or moveable latch) or passive (does not require manipulation by a user) securement mechanism that functions to hold the lead terminal within the lead channel by placing an added force on the terminal that is in addition to a frictional force between those items (including gaskets and seals) with the lead terminal in the fully-inserted position.

According to preferred designs of the implantable lead connection, the specified sealed and secure connection can be produced by a simple "push-only" method of inserting the lead terminal into the lead channel. A "push-Only" method refers to a method that involves only a step of pushing the lead terminal into the channel to attain a fully-inserted position of the lead terminal in the lead channel, after which a user (e.g., surgeon) is not required to further address the lead connection in any manner, such as by performing any additional venting step, any step of manipulating (e.g., opening or closing) a vent, or any step of manipulating a mechanical securing or locking device such as a set screw or the like. Advantageously, any such cumbersome steps can be eliminated, preventing the possibility of a failure by the surgeon to correctly perform the step and preventing any possibility of a potential complication during a surgical procedure that might occur due to the structure, operability, or manipulation of a venting or mechanical securing structure. Fully placing the lead terminal by pushing is the only step required to produce a connection that is sufficiently sealed and secure to be surgically placed implant within a patient.

A lead connection as described herein, and its related methods, can be useful with any type of electronic device with which a secure and reliable sealed electrical connection is desired between a lead terminal and a lead channel. A described lead connection can be particularly useful in a device that would benefit from a sealed connection, such as a portable consumer electronic device or an electronic device designed and intended for use in outside environments, underwater, or in a fluidic (liquid) environment such as internal to a living, mammalian, or human being. Particular devices that benefit from the ease of use, secure connection, and sealed connection features of the present lead connections can be implantable electronic devices including devices useful for cardiac applications (pacemakers and other cardiac stimulating devices), hearing implants, nerve stimulation implants, etc.

Of all of the various known electronic devices, those that include relatively sensitive signal receptors and that require high fidelity signal processing and delivery can especially benefit from the described lead connection, due to the ability to reduce or eliminate feedback effects that can occur upon even minor leakage of a sealed lead connection. Even apart from reduced feedback, however, electronic medical implants and electronic devices more generally will benefit from the improved ease of use of the described vented design, which has the ability to allow a surgeon or non-surgeon user to connect a lead terminal to a lead channel to produce a sealed connection with reduced complication, optionally by a single push of the lead terminal into the lead channel after which the connection is sufficiently secure and sufficiently sealed against fluidic and electrical leakage to allow surgical placement within a patient.

In one aspect, the invention relates to a combination lead terminal and lead channel. The combination includes: a lead terminal comprising a forward end, a distal end, a shaft between the forward end and the distal end, a terminal contact, and a gasket extending around an outer surface of the shaft on a distal side of the terminal contact; a lead channel comprising: a channel wall, a channel contact, an open end, and a closed end, the lead channel adapted to receive the lead terminal. A vent extends through the channel wall from a channel vent hole in the channel to an exterior vent hole. The lead terminal and lead channel are configured for the lead terminal to be inserted through the open end and into the channel and into a fully-inserted position wherein: the terminal contact is electrically engaged with the channel contact; the gasket engages an inner surface of the channel wall to produce a seal; the gasket is located between the open end and the closed end; the channel vent hole is located between the gasket and the open end; and the terminal contact and channel contact are located between the gasket and the closed end.

In another aspect the invention relates to an electronic device that includes a lead channel. The lead channel includes: an open end; a closed end; a channel wall extending between the open end and the closed end; a channel contact located at the channel wall; and a vent extending through the channel wall from a channel vent hole at an inner channel wall surface to an exterior vent hole. The channel vent hole is located between the channel contact and the open end.

In another aspect the invention relates to a method of assembling an electronic medical device. The method includes: providing a combination lead terminal and lead channel as described herein; inserting the lead terminal into the fully-inserted position; and implanting the device in a human patient.

In yet another aspect the invention relates to a method of assembling an electronic medical implant that includes a lead connection between a lead terminal and a lead channel. The method includes: providing a lead channel comprising a channel contact, a channel vent hole, an open end, and a closed end; providing a lead terminal comprising a terminal contact and adapted to engage the lead channel; providing a gasket between the lead channel and the lead terminal; inserting the lead terminal into the lead channel by pushing the lead terminal into a fully-inserted position. In the fully inserted position: the terminal contact is electrically engaged with the channel contact; the gasket engages an inner surface of the channel wall to produce a seal, the gasket is located between the open end and the closed end, the channel vent hole is located between the gasket and the open end, and the terminal contact and channel contact are located between the gasket and the closed end. The method does not include any additional venting step to remove air from channel after the inserting step, and the method does not include any additional securing step to secure the lead terminal within the lead channel, after the inserting step.

DETAILED DESCRIPTION

Figure 1:
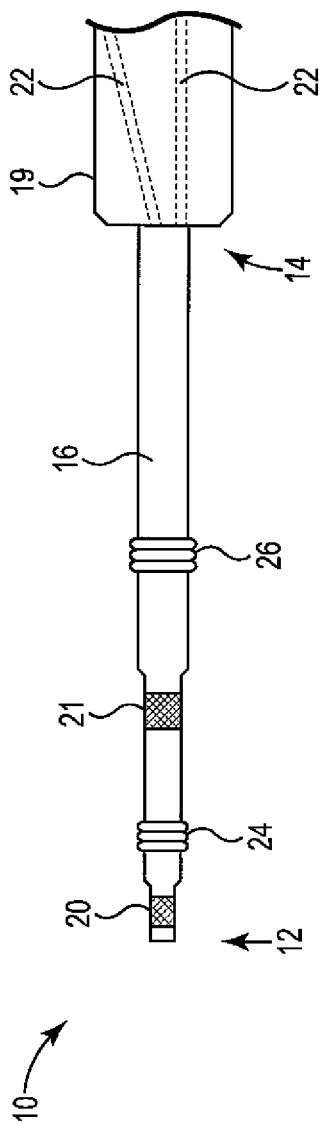
FIG. 1 illustrates an example of a lead terminal as described.

Various electronic devices, machines, computers, manufacturing equipment, consumer electronic devices, medical devices (implantable or otherwise), etc., include electrical connectors that require a seal to produce a fluid (liquid) seal and electrical isolation relative to an external environment. Examples include electrical machines or apparatus that are exposed to outside conditions, weather, underwater use, or use within a fluidic (liquid) environment such as a living body (human, mammalian, etc.). Sealed electrical connections in implantable electronic medical devices, due in part to their ability to be sealed against fluidic and electrical leakage, provide invaluable life-improving or life-extending service to a variety of patients. These devices include electronic hearing implants, pacemakers, defibrillators, other cardiac stimulative devices, and various implantable nerve-stimulation devices that control or improve anatomical functions ranging from hearing, pain control, appetite control, and urinary continence, among others.

Implantable medical devices must be well sealed to prevent liquid fluid from passing into the device, where the fluid might interfere with the electronic functioning of the device. Such implantable devices include a sealed lead connection by which an electronic lead terminal is electrically connected to an electronic processor unit, while also being sealed against electrical and fluid leakages. The sealed lead connection should be one that can be conveniently prepared during a surgical operation, that produces a tight and durable seal that prevents passage of a liquid fluid into the lead connection or device, and that does not exhibit an undue risk of becoming disconnected, even partially, subsequent to surgical implantation. The sealed lead connection should also isolate all electric contacts associated with the lead terminal and the electronic processor from other electrical contacts and from an environment exterior to the implant such as a body of a patient.

An electronic device having a sealed lead connection as described can include an electronic processor unit useful, for example, to receive an electrical input, process the input to produce an electrical output, then transmit the output to an output device, or a combination of two or more of these. The processor unit connects to one or more implantable leads that include a lead terminal that connects electrically to the electronic processor unit, a lead conductor that extends from the lead terminal, and an electrical output or input also electrically connected to the lead conductor. The one or more lead conductor may be any known conductor such as an elongate flexible lead wire extending from the lead terminal to an electronic device such as an electronic input or an electronic output. An electronic input or output connected to the lead conductor may be a transducer, electrode, metal sheet for sensing a heartbeat (pacemaker), driver (e.g., speaker), sensor (e.g., microphone), or another electrical input or output signal generating or signal delivery device.

The processor unit includes electronics and typically a power source such as a battery. The design and general function of the electronics will be suited for the particular type of implantable device, and will differ depending on the type of output, input, and processing the device is intended to produce, which can depend directly on the type of electronic function the implantable device is designed to perform, e.g., as a pacemaker, defibrillator, hearing implant, nerve stimulation implant, etc. Electronics of a pacemaker unit will differ from electronics of a nerve stimulation unit, which will differ from a hearing implant, etc. Each type of electronic processor unit will include an electrical lead connection between the unit and an electrical lead, e.g., a sealed connection between a lead terminal of the electrical lead, and a lead channel of the processor unit.

The implant, typically as part of or adjacent to the electronic processor unit, includes a lead receptor or a header structure that includes a lead channel, including one or more electrical contacts, for receiving a lead terminal. The channel can be in the form of an elongate cylindrical bore having a closed (forward) end, an open (distal) end, and a length between the two ends. The channel can be cylindrical and may exhibit a single diameter continuously along the entire length between the two ends or may include multiple diameters, smaller diameters generally being located toward the forward end. A typical diameter may be in the range from 2 to 10 millimeters, and a typical length between the open end and the closed end may be from about 10 to 75 millimeters. An inner surface of the channel is typically made of a high electrical resistance material such as a polymer, in the form of a smooth surface finished to allow a seal to be formed by placement of a circular gasket within the channel between the inner surface and an outer surface of a cylindrical lead terminal. The channel also, as indicated, includes one or multiple locations at which an electrical contact (channel contact) resides, for electrical connection with an electrical contact of a lead terminal while the lead terminal is in a fully-inserted position. Desirably, a space or "pocket" can be located at or toward the closed end of the lead channel, to increase the volume of the sealed channel.

A lead terminal is an elongate electrical structure that includes at least one electrical contact, and a gasket. Optionally a lead terminal may include multiple conductive electrical contacts, an insulator between any two electrical contacts, and two or more gaskets located at different length-wise positions along the lead terminal. The elongated lead terminal includes a forward end and a distal end. These labels for the ends are arbitrary, but for purposes of the present description the forward end is the end that enters the lead channel first during insertion and the distal end is the end that follows during insertion and that connects to the lead wire. The forward and distal ends of the lead terminal correspond to similar forward (closed) and distal (open) ends of the lead channel.

A useful gasket can be any gasket that is useful to produce a fluid-tight seal between an outer surface of the lead terminal and an inner surface of a lead channel, with the lead terminal in a fully-inserted position. Various gaskets and gasket materials are well known and commercially available, including a variety of pliable, inert polymeric material such as silicone and polyurethane, among other polymeric materials.

An example of a lead terminal is shown at FIG. 1. Lead terminal 10 includes elongate rigid shaft 16, including forward end 12 and distal end 14. Distal end 14 engages lead body 18 and lead conductors 22, shown as conductive wires. Also located along a length of shaft 16 is at least one lead contact (electrical contact) 20 and 21 (shown as shaded regions), as well as one or more gasket 24, 26. Each of lead conductors 22 is in electrical contact at one end with one of lead contacts 20, 21, and is in electrical contact at an opposite end with an electrical input or an electrical output, e.g., an electrical transducer, electrode, sensor (e.g., microphone), speaker, driver, resistor, etc.

In the illustrated example, lead contact 20 and lead contact 21 are situated generally at a forward location along a length of shaft 16 (i.e., on the forward half of shaft 16). Shaft 16 includes three sections of different diameters, the most forward section having the smallest diameter and the most distal section having the largest diameter. Gasket 24 is on the section of shaft 16 having the intermediate diameter. Gasket 26 is on the section of shaft 16 having the largest diameter.

The lead terminal of FIG. 1 is just one example of a lead terminal. Other versions and designs of lead terminals will also be useful according to the present description. Many examples of lead terminals are commercially known and commercially available, some of which are standardized for use in consumer electronic devices and medical implants. A commonly used implantable electrical lead is commercially available under the designation "IS-1," and is used in pacemakers and defibrillators. Other implantable connector designs are referred to and commercially available under the trade designations "VS-1," "VS-1A," "IS-1B," "VS-1B," and "IS-4," any of which can be useful according to the present description. The purpose of these implantable connectors is to electrically connect one or more electrical lead contacts to one or more corresponding electrical contact in a lead channel, while also isolating the different contacts from one another. To accomplish this, connections use a gasket (e.g., a silicone seal) between a lead terminal and a lead channel to prevent fluid ingress and to electrically isolate the different conduction pathways.

The implantable electronic device, generally as part of a header or lead receptor located adjacent to or otherwise in electrical connection with an electronic processor unit, also includes a lead channel for connecting to a lead terminal (e.g., multiple lead channels, one lead channel corresponding to one lead terminal). According to the invention, the lead channel includes a vent in the form of an open (e.g., not closeable, but permanently open) vent (i.e., an open bore or open channel) that extends between an opening (channel vent hole) at an inner surface of the channel, and an exterior location; the vent may be an open bore, channel, or other passage extending through the channel wall from a channel vent hole opening in the channel, to an exterior vent hole.

The channel vent hole may be located at a location along a length of the lead channel on a distal portion of the channel, meaning, for example, at a location between an open end of the channel and a location midway between the open end and the closed end. Alternately, a channel vent hole can be located at a length-wise location of the channel that is between the open end and a distance from the open end equal to ⅓ of the total length of the channel, e.g., at a length-wise location of the channel that is between the open end and a distance from the open end equal to ¼ of the total length of the channel.

The lead terminal and the lead channel are configured so that the lead terminal can be inserted into the channel open end, advanced into the channel, and to finally achieve a fully-inserted position within the lead channel. In the fully-inserted position, a terminal contact is electrically engaged with a channel contact and a gasket engages an inner surface of the channel wall to produce a seal; the gasket is located between the open end of the channel and the closed end of the channel, and the channel vent hole is located between the gasket and the open end of the channel; the terminal contact and channel contact (or two or more sets of corresponding terminal and channel contacts) are located between the gasket and the closed end, within the closed and sealed channel. According to this configuration of the vent, gasket, terminal contact, and channel contact, the lead terminal can be inserted into the lead channel by a surgeon during a surgical procedure, to allow for a useful amount of venting of the channel, and to seal the channel with all electrical contacts situated within the sealed channel, meaning on a forward side of at least one sealing gasket. With the venting, the insertion force associated with pushing the lead terminal into the lead channel is reduced relative to an unvented channel, because the venting reduces the amount of air that is trapped within the channel by the gasket as the lead terminal is advanced within the channel. With a reduced amount of air being trapped within the sealed channel, the level of pressurization inside the sealed channel is reduced, while some level of pressurization still does occur and the interior channel pressure is greater than ambient (atmospheric) pressure. The risk of the lead terminal moving within the channel (e.g., partially disconnecting) after surgical placement is reduced due to the lower level of pressurization within the sealed channel. The need for a mechanical securement feature such as a set screw is reduced or eliminated.

The vent can be any vent useful to allow air to flow out of the lead channel as the lead terminal is inserted into (by pushing) and advanced along a length of the lead channel. The vent can optionally be one that may be opened and closed by a user (e.g., surgeon), one that allows for one-way passage of air such as a "check valve," one that includes a polymeric barrier with an opening therethrough (e.g., a self-sealing membrane), etc. But, as may be preferred for simplicity of design and use, the vent can advantageously and preferably be in the form of a permanently open and non-closeable bore that extends from an opening at an interior surface the lead channel, to an exterior, that does not include any opening or closing mechanism, and that is in the form of an always-open unobstructed channel. Unlike vents that require or allow for manipulation by being alternately opened and closed, venting by use of the an always-open unobstructed channel allows venting to occur automatically upon inserting and advancing the lead terminal into the lead channel without any other required step of opening or closing the vent, inserting a needle through a barrier membrane, or removing a PTFE tube, etc. Also, unlike implantable lead connections that include a mechanical securing or locking mechanism that must be tightened or actuated after placement of a lead terminal into a lead channel, embodiments of the described lead connection need not require any such mechanism, thereby eliminating a step of actuating or manipulating the mechanical securing or locking mechanism during a surgical procedure, such as by tightening a set screw. Advantageously, according to certain embodiments of the described sealed lead connections, after a push step by which the lead terminal is inserted into the channel and advanced within the channel to achieve a fully-inserted position, no additional step relating to venting or securing the lead channel or lead terminal is required to prepare the lead connection between the lead terminal and the lead channel for surgical placement within a patient.

Figures 2, 3A:
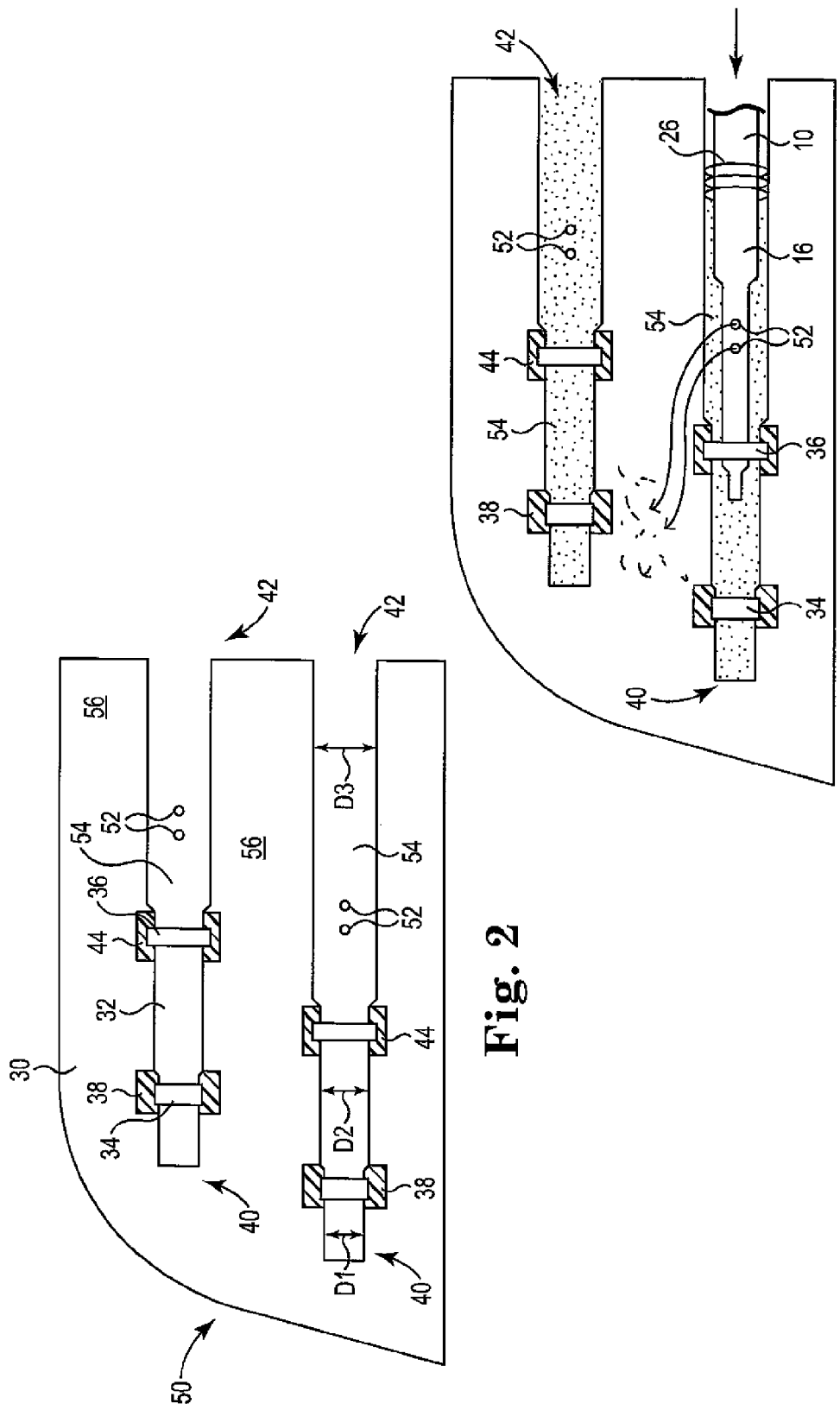
FIG. 2 illustrates an example of a lead channel as described.
FIGS. 3A and 3B illustrate an example of a lead terminal and lead channel as described.

FIG. 2 illustrates an example of a lead channel as part of a receptor or header connected to an electronic processor unit of an implant. Header 50 shows two lead channels, although a header or implantable device may include fewer (only one) or more. Header 50 is connected to an electronic processor unit (not shown) of an implant. Lead channel 54 includes and extends between open (distal) end 42 and closed (forward) end 40. An inner surface of channel 54 includes a length and optionally (also as illustrated) multiple diameters. Vent holes 52 include and extend between one opening at an inner surface of channel 54 and a second opening at an exterior of header 50. As illustrated, vent holes can be open bores extending between the two openings, through channel wall 56. At least one (optionally two, three, or more) electrical contact (channel contact) 38, 44, is located at a location on the interior of channel 54, and is in electrical communication with the electronic processor unit (connection not shown). Optionally and as illustrated, lead channel 54 can include one or more passive securing mechanisms 34, 36 such as a detent (ball-and-spring type, annular spring type, or the like) that places added frictional force on a surface of a lead terminal in a fully-placed position within the lead channel, to further reduce the risk of subsequent movement of a lead terminal within lead channel 54. As shown at FIG. 2, header 50 includes two lead channels, each of which can be vented as described herein. Also optionally and as illustrated, lead channel 54 can include sections of different diameters. As shown, D1 is smaller than D2, which is smaller than D3.

In use, the vented channel allows an amount of venting of the lead channel during insertion of the lead terminal into the lead channel, during at least a portion of the insertion step during which a gasket (e.g., 26 on the lead terminal) remains on a distal side of the vent opening within the channel. During that portion of the push step, at least a portion of the amount of air that is located at the interior of the channel and inside of (on a forward side of) a sealing gasket (e.g., 26) can be pushed through the vent and out of the interior volume of channel 54. During a later portion of the push step, after the gasket passes the location of the vent opening (e.g., 52) along the length of the channel, air located at the interior of the channel and inside (on a forward side of) the sealing gasket is no longer vented, but does become compressed. While some amount of air is compressed to produce a pressure increase, the volume of air that does become compressed in the sealed channel is reduced relative to a channel in which a volume of air that corresponds to the total channel volume would be compressed (e.g., in the absence of any venting).

Desirably and according to various embodiments of vented lead channels as described herein, a level of pressurization within the vented and sealed lead channel, with the lead terminal in the fully-inserted position, can be below a level of pressurization that would create an unacceptable risk of the lead terminal moving out of the fully-inserted position after implantation, e.g., separating, decoupling, or disconnecting or otherwise even partially separating from or moving within the lead channel. Optionally, as described herein, the sealed implantable lead connection can also if desired or necessary be mechanically held in the lead channel by a securing or locking mechanism to achieve or surpass a useful or desired level of risk of movement (e.g., dislodgement) of the fully-inserted lead terminal. According to certain embodiments of implantable connectors, any such mechanical securing or locking mechanism can preferably be one that does not require any manipulation by a surgeon during a surgical procedure, i.e., a "passive" mechanism, such as an annular spring or other detent-type of mechanism, as compared to an "active" type of locking mechanism such as a set screw.

In more detail, certain preferred embodiments of lead connections can exclude any form of mechanical securing or locking mechanism, especially active locking mechanisms, that involve placing a mechanical force on a lead terminal to prevent movement of the lead terminal relative to the lead channel. For example, certain implantable lead connections can exclude the presence of any form of "active" securing mechanism that requires manipulation by a surgeon, such as a set screw capable of being manipulated (e.g., tightened) by a surgeon to contact the lead terminal to frictionally secure the lead terminal at a location within the lead channel. Likewise, a lead connection can exclude other types of active frictional securement mechanisms that are manipulated by a surgeon during use, such as any of a threaded engagement; a moveable ratchet, latch or detent; or another type of mechanical frictional device that is manipulated by a user (e.g., surgeon) to increase an amount of friction between the lead terminal within the lead channel (relative to the amount of friction present between the lead shaft, lead channel inner surface, and one or more gasket).

Embodiments of the implantable lead connection can also optionally include or exclude a passive frictional securing mechanism that does not require any manipulation by a user (e.g., surgeon). One example of a passive securing mechanism is an annular spring placed between an inner surface of a lead channel and an outer surface of a lead terminal, such as at opposing grooved or shouldered surfaces. The groove and annular spring arrangement can increase a frictional force that retains the lead terminal within the lead channel, with the lead terminal in a fully-inserted position, e.g., to further reduce the risk of the lead terminal moving within the lead channel. Other examples of passive mechanisms can include a ball-and spring detent, a "snap-fit" engagement, or other mechanism that increases friction without any required manipulation by a surgeon or user. An "annular spring" is a spring that includes a circular axis defined by the center of the spring winding. An annular spring in a lead channel can be situated within a groove in the lead channel, and the groove in the channel and the location of the annular spring can be adjacent to a groove or other surface or shoulder of the lead terminal as the lead terminal is situated in a fully-inserted position, to increase frictional force between the lead channel and lead terminal. Optionally, two such annular springs can be included in an implantable lead connection at different locations along a length of a channel. The annular springs can be part of the electrical contact (see FIG. 2) or may be used solely for mechanical fixation.

As shown at FIG. 3A, a lead terminal (e.g., 10) can be inserted into open end 42 of a channel 54 and advanced toward closed end 40. Gasket 26 produces a circular seal between an outer surface of shaft 16 and an inner wall surface of channel 54. As lead terminal 10 is pushed and advanced in a forward direction (see arrow) toward closed end 40, with gasket 26 located between open end 42 and the location of vents 52, a portion of the air contained in lead channel 54 forward of gasket 26 leaves the interior space of channel 54 through one or more of vents 52. The venting of that portion of air from the interior of channel 54 reduces the insertion force required to push lead terminal 10 into lead channel 54, and also reduces the amount of air contained within channel 54 on the forward side of gasket 26 with lead terminal 10 in its fully-inserted position (see FIG. 3B).

Figure 3B:
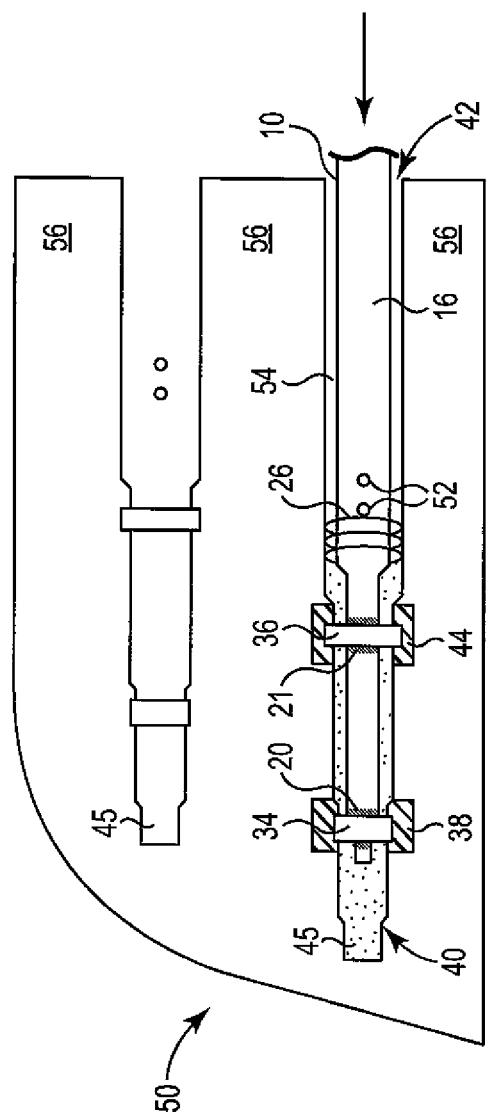

The reduced amount of air contained in sealed channel 54 results in a reduced pressurization of the interior of channel 54 as lead terminal 10 is advanced in the forward direction (shown by arrow at FIG. 3A) and to a fully-inserted position. FIG. 3B shows a later stage of an insertion or "pushing" step, during which terminal 10 has been advanced farther in the forward direction and has achieved a fully-inserted position. In the illustrated fully-inserted position, terminal contacts 20, 21 are in electrical engagement with channel contacts 38, 44; gasket 26 is located at an outer surface of lead terminal 10 and engages an inner surface of lead channel 54 to produce a circumferential seal at a location of gasket 26 and sealing the lead channel on the forward side of gasket 26; gasket 26 is located between open end 42 and a closed end 40; one or more channel vent hole 52 is located between gasket 26 and open end 42; one or more terminal contact and channel contact are located between gasket 26 and closed forward end 40; a channel or shoulder structure (not shown) about a circumference of lead terminal 10 aligns with one or more passive securing mechanism (e.g., annular spring) 34, 36, to increase a frictional force between lead terminal 10 and lead channel 54; no electric contact (terminal contact or channel contact) is located between gasket 26 and open end 42.

Also as illustrated, gasket 24 (which is optional) is located at an outer surface of lead terminal 10 at a length of channel 54 that exhibits reduced diameter D3. Gasket 24 engages an inner surface of lead channel 54 at the portion of channel 54 having diameter D2 to produce a circumferential seal. At more distal locations along the length of channel 54, i.e., at locations of diameter D3, gasket 24 passes through the larger diameter portion of channel 54 without creating a seal, due to a relatively smaller diameter of gasket 24 compared to D3. In alternate embodiments (not illustrated), multiple gaskets located at different locations along a length of a lead terminal 10 may have the same diameter, which matches an inner diameter of a lead channel to produce a seal. Each of the gaskets can sequentially pass a channel vent hole 52 to become located forward of vent hole 52 with the lead terminal located at a fully-inserted position.

FIG. 3B shows optional pocket 45, which is an oversized space located at a forward location (e.g., forward end 40) within channel 54. Pocket 45 is located at forward end 40 of channel 54, which receives forward end 12 of terminal lead 10. Pocket 45 is a sealed space at closed (forward) end 40 of channel 54 that is larger than necessary to physically fit forward end 12 of terminal lead 10. The purpose of oversized space or "pocket" 45 at forward end 40 of channel 54 is to provide an increased volume of space at forward end 40, for containing an amount of compressed air contained in channel 54 forward of gasket 24, with lead terminal 10 in a fully-inserted position. While advancing lead terminal 10 into a terminal channel, gasket 24 creates a seal upon contacting an inner wall of channel 54 at the portion of channel 54 having diameter D2. When gasket 24 is advanced along the length of this portion of channel 54, air contained in the space forward of gasket 24 becomes compressed. If the volume of space in channel 54 that is forward of gasket 24 is too small, the compressed air contained in that space would be pressurized to possibly an excessive level. A larger volume of space provided by pocket 45 to contain the compressed air forward of gasket 24 will prevent an unacceptably high level of pressure in that portion of channel 54, without the need for venting that space. The size and diameter of pocket 45 can be any that are useful. As illustrated at FIG. 3B the diameter of pocket 45 is smaller than diameter D1 (see FIG. 2). Alternately, the diameter of pocket 45 can be the same as diameter D1.

The illustrated and described lead connections differ from previous lead connection designs for a variety of useful and potentially advantageous reasons. For example, placement of a vent of a terminal channel on a distal side of a gasket and on a distal side of an electrical contact (with the lead terminal in the fully-insertion position) allows for venting followed by sealing of the channel interior (containing the electrical contact) during a single pushing step. The described vent between the lead channel and the exterior need not be moveable (e.g., openable and closeable) or otherwise manipulated during use. In certain embodiments (and as illustrated) the vent can be an open and unobstructed channel that remains open before and after a pushing step to advance the lead terminal and place the lead terminal in a fully-inserted position in the lead channel, and also remains open during surgical placement of the assembled lead connection into a patient, as well as long after implantation subsequent to the surgery. This reduces the complexity of the structure and of the preparation and use of the lead connection.

Certain described designs allow for embodiments of lead connections that can exhibit improved ease of use by allowing a lead terminal to be placed in a fully-inserted position by a single pushing step with no other venting or securement step. A surgeon, during a surgical procedure (or any other user of an implantable or non-implantable device), is able to make a secure and vented and sealed lead connection by just a single push of the lead terminal into the lead channel. Because the lead channel does not require any additional venting or venting steps, e.g., after the lead terminal achieves the fully-inserted position, the vent is not required to be either opened or closed or otherwise manipulated during or after placement. Also optionally and preferably, no manipulation of a mechanical securement or locking mechanism is required. The lead connection can be ready to be placed within a patient after the single pushing step. There is no additional requirement for a performing surgeon to manipulate any portion of the implant to either reduce a level of pressurization within the sealed channel or to increase a frictional force holding the lead terminal in place in the lead channel.

Embodiments of the described electrical connection can be useful in any type of electrical device that includes a connection between a lead terminal and a lead channel. Particular devices that can benefit from the described connection can be implantable electronic devices. Much of the following description will be in the context of a hearing implant, but, as indicated, the inventive structures and methods can be useful with any type or medical, non-medical, implantable, or non-implantable electrical or electronic devices.

Hearing implants useful to improve hearing in a patient include those referred to commonly as partial middle ear (P-MEI) hearing implants and total middle ear (T-MEI) hearing implants. These implants are designed to be surgically placed and functionally connected to a middle ear space. A P-MEI or T-MEI hearing implant may be installed to assist the human auditory system in converting acoustic energy contained within sound waves into electrochemical signals delivered to the brain and interpreted as sound. Certain types of these devices can include an electronic processor unit, conductive leads, and transducers located within the middle ear and in contact with an auditory element. Vibrations received by an input transducer are processed, generally with amplification, to produce an output vibration at an output transducer. The output transducer causes vibration of an auditory element to allow the patient to perceive the signal as an audible sound. The input signal is generally amplified and filtered by electronics in the electronic processor unit, and then transmitted to the electromechanical output transducer, which, in turn, vibrates a bone in the ossicular chain of middle ear 35, such as stapes 180 or malleus 140. The amplifier, filter, and other components of the electronic processor unit are typically located away from the transducers implanted in the middle ear. These electronic items typically include a voltage source such as a battery, filters, compression circuits, and other components.

A typical hearing implant can include a sensor (i.e., input or microphone) assembly, a driver (i.e., output or speaker) assembly, electronic processor unit, conductors between the input and output assemblies and the processing unit, and mounting devices for placing the components into a functional relationship with relevant anatomy of a patient's inner ear. For example, a trans-canal implant procedure may place portions of the hearing implant at locations of the auditory canal and the tympanic membrane, preferably without the need for mastoid surgery.

Figure 4:
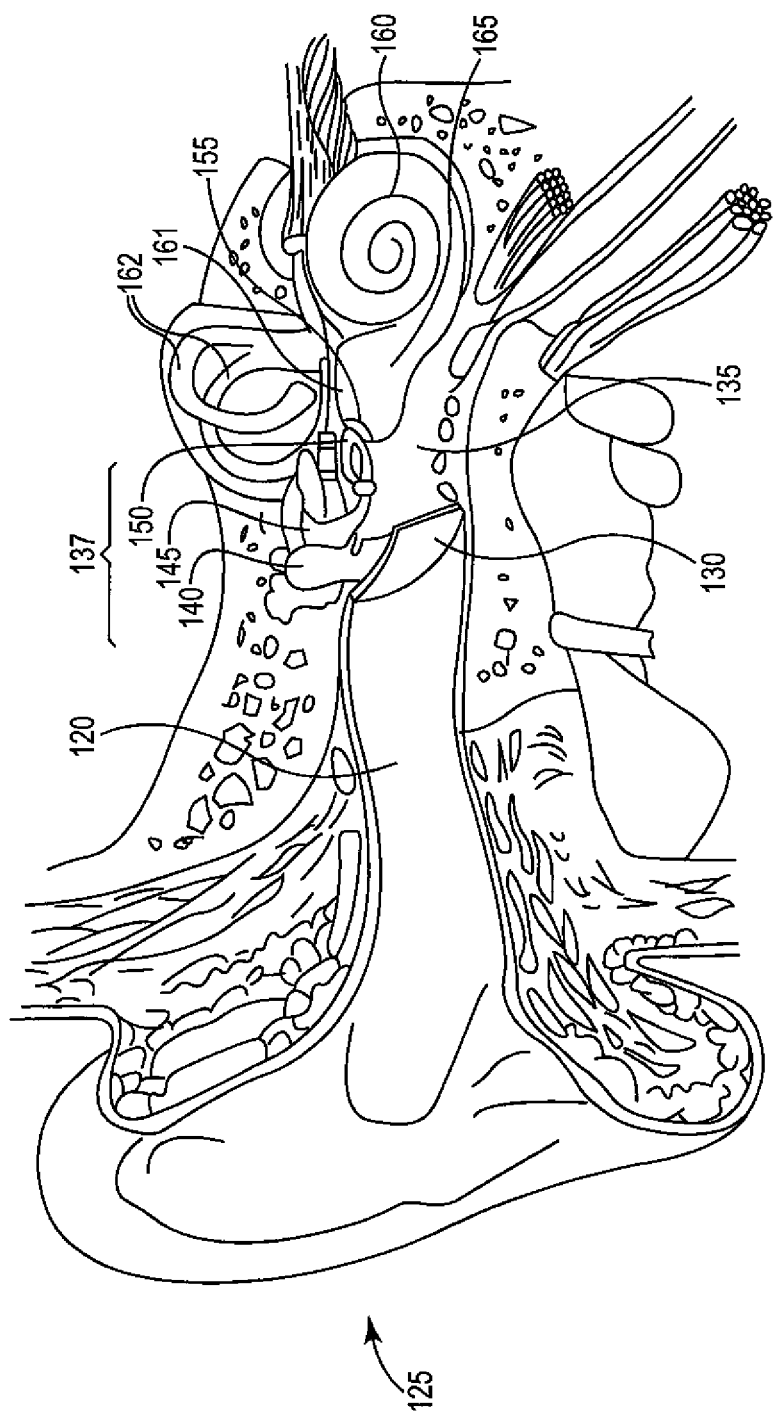
FIG. 4 illustrates anatomy of a middle ear.

Anatomy relevant to hearing implants is shown at FIG. 4, showing features of the human auditory system. Sound waves are directed into an external auditory canal 120 by an outer ear (pinna) 125. The frequency characteristics of the sound waves are slightly modified by the resonant characteristics of the external auditory canal 120. These sound waves impinge upon the tympanic membrane (eardrum) 130, interposed at the terminus of the external auditory canal, between it and the tympanic cavity (middle ear) 135. Variations in the sound waves produce tympanic vibrations. The mechanical energy of the tympanic vibrations is communicated to the inner ear, including the cochlea 160, vestibule 161, and semicircular canals 162, by a sequence of articulating bones located in the middle ear 135. This sequence of articulating bones is referred to generally as the ossicular chain 137. Thus, the ossicular chain transforms acoustic energy at the eardrum 130 to mechanical energy at the cochlea 160.

The ossicular chain 137 includes three primary components: a malleus 140, an incus 145, and a stapes 150. The malleus 140 includes manubrium and head portions. The manubrium of the malleus 140 attaches to the tympanic membrane 130. The head of the malleus 140 articulates with one end of the incus 145. The incus 145 normally couples mechanical energy from the vibrating malleus 140 to the stapes 150. The stapes 150 includes a capitulum portion, comprising a head and a neck, connected to a footplate portion by means of a support crus comprising two crura. The stapes 150 is disposed in and against a membrane-covered opening on the cochlea 160. This membrane-covered opening between the cochlea 160 and middle ear 135 is referred to as the oval window 155. Oval window 155 is considered part of cochlea 160 in this patent application. The incus 145 articulates the capitulum of the stapes 150 to complete the mechanical transmission path.

Normally, prior to surgical placement of a hearing implant, tympanic vibrations are mechanically conducted through the malleus 140, incus 145, and stapes 150, to the oval window 155. Vibrations at the oval window 55 are conducted into the fluid filled cochlea 160. These mechanical vibrations generate fluidic motion, thereby transmitting hydraulic energy within the cochlea 160. Pressures generated in the cochlea 160 by fluidic motion are accommodated by a second membrane-covered opening on the cochlea 160. This second membrane-covered opening between the cochlea 160 and middle ear 135 is referred to as the round window 165. Round window 165 is considered part of cochlea 160 in this patent application. Receptor cells in the cochlea 160 translate the fluidic motion into neural impulses which are transmitted to the brain and perceived as sound. However, various disorders of the tympanic membrane 130, ossicular chain 137, and cochlea 160 can disrupt or impair normal hearing.

Hearing loss due to damage in the cochlea is referred to as sensorineural hearing loss. Hearing loss due to an inability to conduct mechanical vibrations through the middle ear is referred to as conductive hearing loss. Some patients have an ossicular chain 137 lacking sufficient resiliency to transmit mechanical vibrations between the tympanic membrane 130 and the oval window 155. As a result, fluidic motion in the cochlea 160 is attenuated. Thus, receptor cells in the cochlea 160 do not receive adequate mechanical stimulation. Damaged elements of ossicular chain 137 may also interrupt transmission of mechanical vibrations between the tympanic membrane 130 and the oval window 155.

Hearing implants have been developed to apply various approaches to compensate for hearing disorders. For example, cochlear implant techniques implement an inner ear hearing aid system. Cochlear implants electrically stimulate auditory nerve fibers within the cochlea 160. A typical cochlear implant includes an external microphone, an external signal processor, and an external transmitter, as well as an implanted receiver and an implanted single channel or multichannel probe. Recently, research has been directed toward fully implantable cochlear implants that include an implantable microphone or implantable sensor instead of the external processing unit. The presently-described lead connections can be useful with any of these or other types of implantable hearing devices.

A particularly desired class of implantable hearing systems includes those configured for disposition principally within the middle ear 135 space. In middle ear implantable (MEI) hearing systems, an electrical-to-mechanical output transducer couples mechanical vibrations to the ossicular chain 137, which is optionally interrupted to allow coupling of mechanical vibrations to the ossicular chain 137.

One example of a partial middle ear implantable (P-MEI) hearing system having an electromagnetic output transducer comprises: an external microphone transducing sound into electrical signals; external amplification and modulation circuitry; and an external radio frequency (RF) transmitter for transdermal RF communication of an electrical signal. An implanted receiver detects and rectifies the transmitted signal, driving an implanted coil in constant current mode. A resulting magnetic field from the implanted drive coil vibrates an implanted magnet that is permanently affixed only to the incus.

Figure 5:
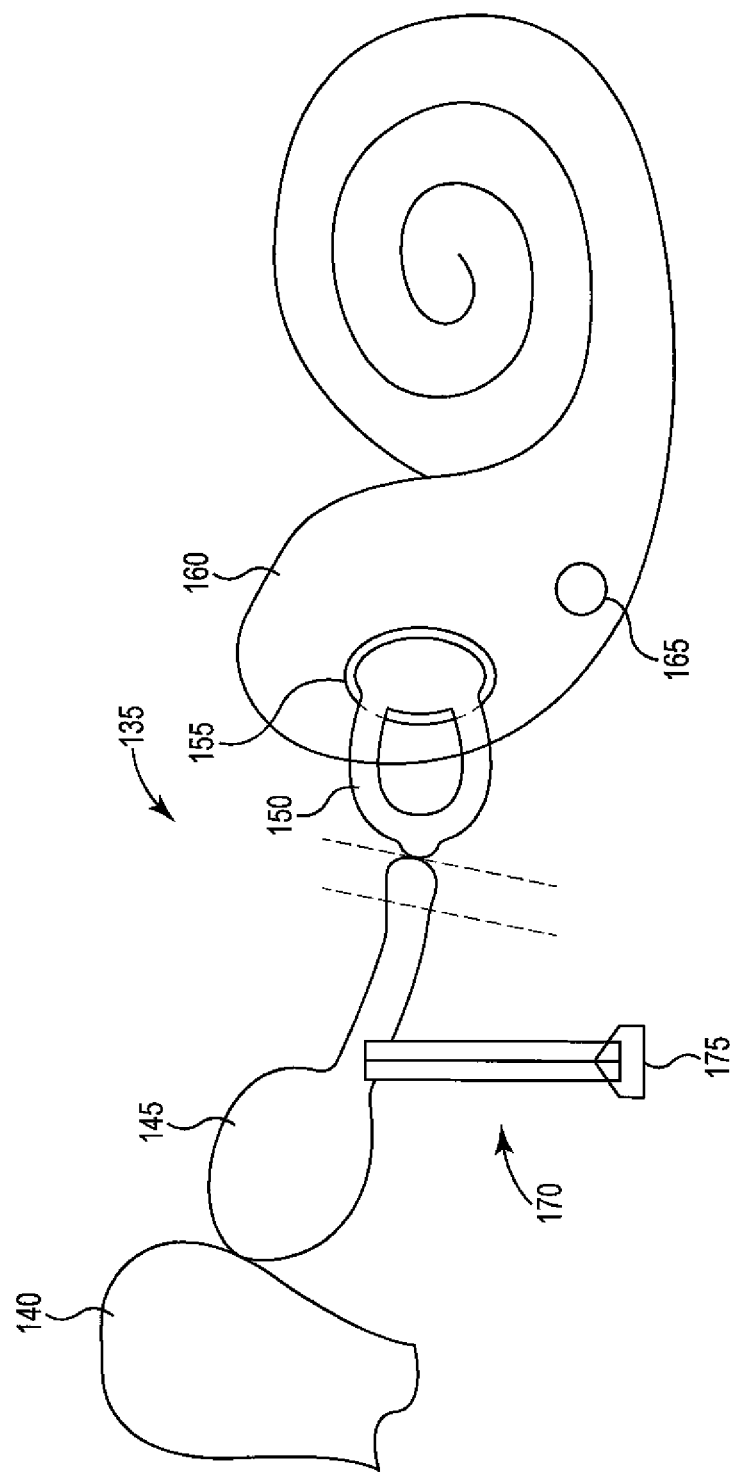
FIGS. 5 and 6 illustrate anatomy of a middle ear and examples of components of an implantable medical device as described.

FIG. 5 is a generalized illustration of a transducer 170 cantilevered at its proximal end from a housing 175 mounted within a middle ear 135. A distal end of the transducer 170 is mechanically coupled to an auditory element to receive or effect mechanical vibrations when operating as an input or output transducer, respectively. For example, to receive mechanical vibrations as an input transducer, transducer 170 may be coupled to an auditory element such as a tympanic membrane 130, malleus 140, or incus 145. In another example, to effect vibrations as an output transducer, transducer 170 may be coupled to an auditory element such as incus 145, stapes 150, oval window 155, round window 165, vestibule 161, or semicircular canal 162. FIG. 5 also shows that incus 145 may be disarticulated from stapes 150 (indicated by dotted lines) in certain configurations.

Figure 6:
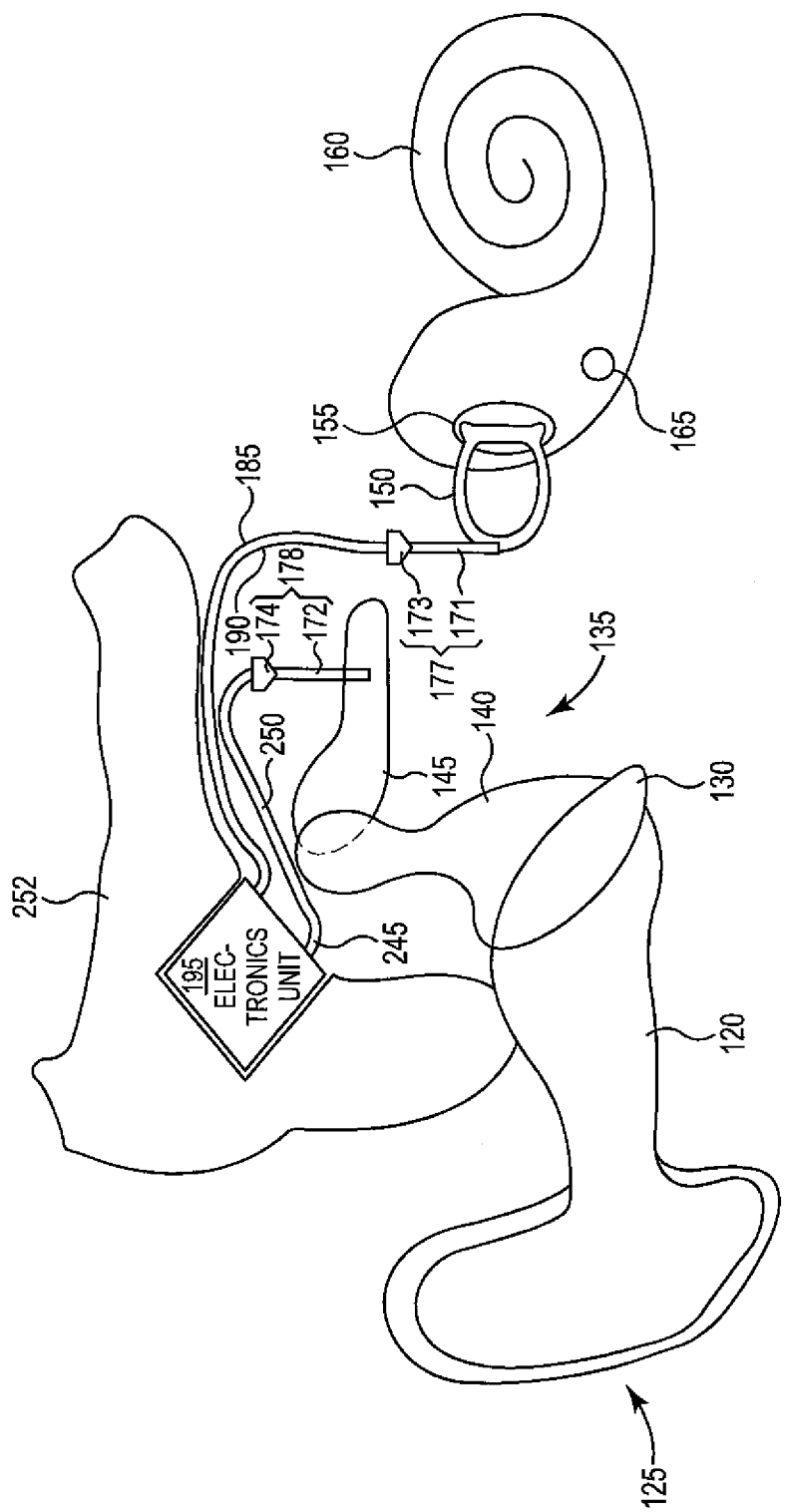

FIG. 6 illustrates generally a cross-sectional view of a T-MEI hearing implant system. Electromechanical input transducer 172 is mounted within middle ear 135 via housing 174, forming the sensing assembly 178 portion of the T-MEI hearing aid system. Electromechanical input transducer 172 is coupled by any known attachment technique at its distal end to an auditory element such as malleus 140, incus 145, or tympanic membrane 130. As shown, vibrations of incus 145 at the distal end of electromechanical input transducer 172 cause vibratory displacements of the electromechanical input transducer 172. As a result, an electrical signal is generated and transmitted through respective lead wires 245 and 250 to electronics unit 195.

Also illustrated at FIG. 6 is an electromechanical output transducer 171 mounted within middle ear 135 via housing 173, forming a driver assembly 177 portion of the T-MEI hearing aid system. Electromechanical output transducer 171 is coupled at its distal end to middle ear 135 only through an auditory element such as stapes 150, incus 145, oval window 155, round window 165, vestibule 161, or semicircular canals 162.

Electromechanical output transducer 171 is secured to stapes 150, for example, by any known attachment technique, including biocompatible adhesives or mechanical fasteners. Electronics unit 195 couples an electrical signal through lead wires 185 and 190 to any convenient respective connection points on housing 173. In response to electrical signals received from electronics unit 195, the electromechanical output transducer 171 generates and mechanically couples vibrations to stapes 150. The vibrations coupled to stapes 150 are in turn transmitted to cochlea 160 at oval window 155.

Figure 7:
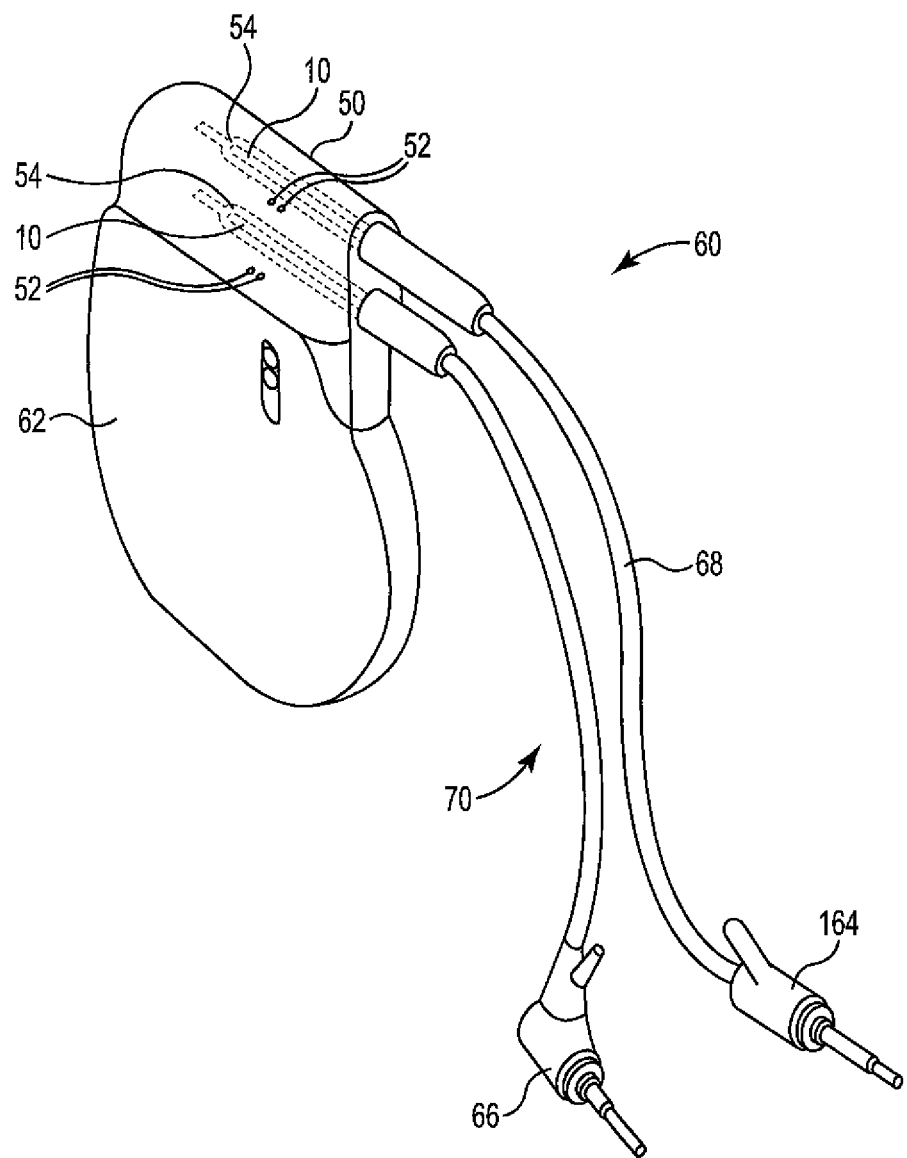
FIGS. 7 and 8 illustrate examples of electronic devices as described.

FIG. 7 is a perspective view of an electronic medical implant according to the invention, as described generally or specifically herein, in the form of hearing implant 60 that incorporates at least one (two as illustrated) implantable lead connection as described herein. Hearing implant 60 includes an electronic processor unit 62, a driver (e.g., speaker) 64 and a sensor (e.g., microphone) 66. Driver 64 and sensor 66 are coupled to electronic processor unit 62 via leads 68, 70 respectively. Hearing implant 60 is intended to be implantable in a human being. In particular, implant 60 is intended to help improve the hearing of a human being with mild to severe sensorineural hearing loss. Sensor 66 may be attached to the malleus or incus bone, and the driver 64 may be attached to the stapes in the middle ear. Electronic processor unit 62 may be implanted in the skull, preferably behind the ear, and includes a sound processor (not shown) and battery (not shown).

Implant 60 may use the ear drum 130 as a microphone, picking up natural sounds through ear canal 120. The sensor 66 may be adapted to pick up vibrations from the eardrum 130, malleus 140, or incus 145, and convert the vibrations into an electrical signal that is sent to unit 62 via lead 70, and its associated lead connection, with lead terminal 10 and lead channel 54. Unit 62 filters and amplifies the electrical signal and send the processed signal to driver 64 via lead 68, via the second illustrated lead connection and a second lead terminal 10 and second lead channel 54. Unit 62 is capable of being programmed to customize for the particular human being in which the system 60 is implanted. Unit 62 also houses a battery (not shown) to power the system. Driver 64 may be coupled to the stapes 150 or oval window 155. Driver 64 converts electrical signals received from the unit 62 into mechanical vibrations that in turn vibrate the stapes 150 or oval window 155.

The inventive structures and method can be useful in conjunction with any surgical method for placing a medical implant. According to certain embodiments of devices and surgical procedures, an implantable lead connection can be prepared by a single step of inserting a lead terminal into a lead channel, as described, with no additional manual step by a surgeon of manipulating the device for reducing pressure within the canal or increasing friction between the lead terminal and lead channel. After the single push insertion step, the surgeon can place the implantable lead connection in the patient and have no need to thereafter address the security, seal, or pressure of the implantable lead connection. The implantable lead connection may be a component of a hearing implant, a pacemaker, a defibrillator, a nerve stimulation device, or any other implantable electronic device.

Certain surgical methods with which the presently described implantable lead connections may be useful include minimally invasive methods of placing a hearing implant and implant components (e.g., sensing and/or driver or a mounting assembly for supporting one or more sensing/driving assemblies, for example) within a middle ear space. See, e.g., U.S. Pat. No. 6,755,778 to Kroll and U.S. Pat. No. 7,297,101 to Neisz et al.

Accordingly, certain embodiments of surgical placement methods for a lead connection as described include forming a low profile entry slit or hole in a tympanic membrane 130. A mounting assembly may then be inserted into and through the slit or hole in tympanic membrane 130. The mounting assembly may then be mounted against a wall of the middle ear space 135, for example. In some embodiments, various portions of a hearing implant, such as those shown at FIGS. 5 and 6, may be implanted in a middle ear space via tympanic membrane 130, and may thereby avoid the need for performing a mastoidectomy. After insertion and installation of hearing aid components through a slit or hole in the tympanic membrane, tympanic membrane 130 will heal appropriately. According to alternate steps of a useful surgical method, tympanic membrane 130 may be "lifted," i.e., removed temporarily, to facilitate placement of hearing aid components within the middle ear space. Upon completion of placement and installation, the tympanic membrane may be reattached, for example.

Of course a hearing implant or other medical implant can be surgically placed using any useful placement steps and any positioning. Alternate methods of access of an inner ear may be combined with the above-described trans-canal access approach. For example, an at least partial mastoidectomy may be used to place a driver assembly in a middle ear location suited for stimulating the incus or malleus head, while a trans-canal approach may be used for placement of a sensing assembly in a suitable location, such as in the cavity between the tympanic membrane and the malleus, for example.

According to the invention, a useful method and implant can include an implantable lead connection as described, and steps of preparing the connection as described, preferably including a single push step of connecting a lead terminal to a lead channel, to the exclusion of any added step required to connect the two items or to reduce an internal pressure of the sealed lead channel.

Figure 8:
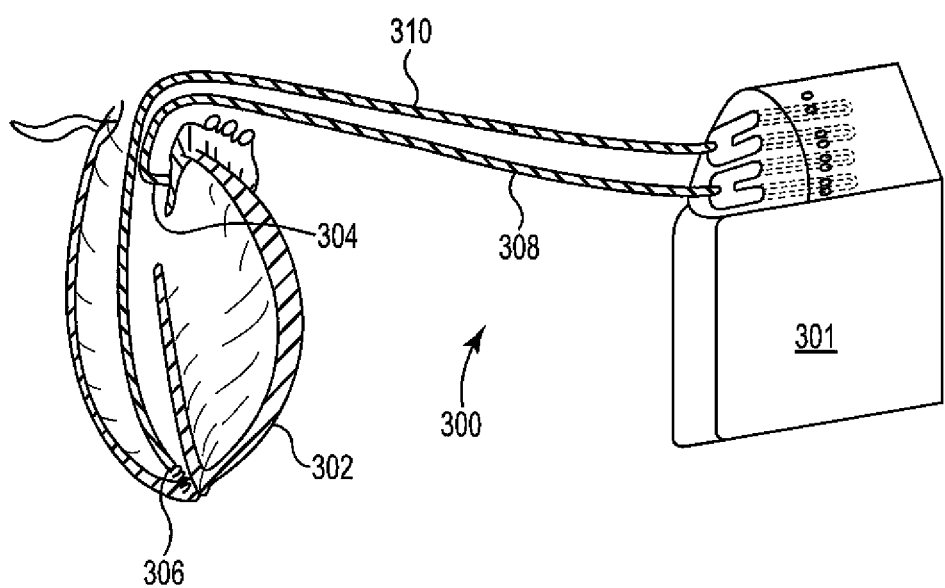

The described implantable lead connection is useful with any of the described hearing implants, any other types of hearing implants, and any other type of electronic device, implantable or otherwise, that includes an electrical connection that is desirably sealed, secure, and easy to use. The electronic device may be an implant such as any of those presently known or future-developed, useful to monitor or control cardiac rhythm, e.g., a pacemaker, defibrillator, or the like. FIG. 8 illustrates an implantable lead connection as described, incorporated into pacemaker device 300. FIG. 8 is a perspective view of pacemaker 300, which can be surgically placed in a patient to control cardiac rhythm of heart tissue 302. Pacemaker 300 includes electronic processor unit 301, a first electronic output or electronic sensor 304, and a second electronic output or sensor 306, either of which may include a sensor or output electrode. First output or sensor 304 and second output or sensor 306 are coupled to unit 301 via leads 308 and 310, respectively. Unit 301, in conjunction to a sensor an output 304 and 306, monitors for a regular heartbeat and, if necessary, stimulates heart tissue 302.

Various electronic devices, e.g., electronic medical implants, are useful with the described vented lead connection. Any of these electronic devices can potentially benefit from the described implantable lead connection, because certain advantages of the lead connection will apply to all types of electronic devices. One such advantage is the ease-of-use advantage, by which the scaled lead connection is easier to assemble compared to certain previous sealed lead connections. Embodiments of the described lead connections can be assembled by methods that require fewer steps—and therefore involve reduced complication and reduced risk of a device malfunction or user error—as compared to previous lead connections, such as by eliminating the need for a specific venting step (such as by placing a core-less needle through a self-sealing membrane), a securing or tightening step (such as a step of tightening a set screw), or a vent removal or closing step (such as a step of removing a PTFE tube that allows air to escape past a sealing gasket during insertion of a lead terminal into a lead channel). While this ease-of-use advantage pertains to a broad range of devices that include a sealed electrical lead connection, e.g., implantable electronic connections, certain other useful or advantageous features of the vented and sealed implantable lead connections as described herein can be particularly useful for certain types of electronic devices.

In general, devices with which the described vented implantable lead connections can be particularly useful or advantageous include electrical devices that include electrical capabilities that involve one or more of: a high level sensitivity of an electrical input, a high level fidelity of receiving a signal input, signal processing that includes amplification of an input signal to produce an output signal, or a high level fidelity of the signal processing and the signal output. This includes hearing implants, but does not necessarily include other general types of electronic medical implant such as nerve stimulation devices, pacemakers, and defibrillators.

A hearing implant requires a highly sensitive input such as a microphone useful to detect sound signals over a range of frequencies and amplitudes, including low amplitude signals. To improve the hearing of a patient in any of varied conditions and environments, the sensor must be continuously on and receptive, must be capable of identifying even low volume signals with high fidelity in conditions of low and high volume signals, and must be able to receive and transmit the input signal with high fidelity to a signal processor. Once a signal is received by the signal processor, the processor must generally amplify the signal with high fidelity, and the signal must be transmitted with high fidelity to a driver (e.g., speaker). Along with all of these functions, the device must work with a minimum or no discernible electromagnetic feedback between the speaker and the microphone.

An electronic lead connection as described can be useful in an implantable hearing device that has sensitivity and fidelity performance that are at least sufficient for performing the function of receiving, processing, and delivering sound signals to a patient at minimum levels useful for a hearing implant and preferably at even higher levels of sensitivity and fidelity. An implant of the invention using an implantable lead connection as described is especially useful in applications that have a low voltage input and a low voltage output, a high level of signal gain, or require a low level of distortion. As an example of a performance feature of a hearing implant, which includes circuitry that includes an amplifier, a hearing implant generally provides 5 to 40 dB of acoustic gain, e.g., 10 to 30 dB of acoustic gain, over a frequency range 250-8000 Hz (the acoustic gain being measured as an average of the frequency range). The electrical gain provided by the device may need to be equal to or greater than the acoustic gain realized by the patient. The implant must be able to provide this level of gain without entering electrical feedback. If electrical feedback is encountered, the electrical amplification must be reduced, subsequently reducing the acoustic gain received by the patient. Hearing implants that include an implantable sealed lead connection as described can be capable of providing a useful level of signal gain and of performing as a hearing implant in a patient for an extended period of time without exhibiting an undue level of feedback between the speaker and microphone.

The present lead connection can reduce or eliminate the possibility of electronic feedback compared to certain previous lead connection designs. Previous lead connection designs, for example those that involve a self-healing membrane to allow venting by use of a set screw or a non-coring needle, allow for the risk of liquid or electronic leakage through the self-sealing membrane. In practice, self-sealing membranes often allow for at least a very small amount of fluid leaking, which allows for electrical leaking. Even a very small amount or electrical leaking between contacts of a hearing implant can allow for undesired feedback, and even a very low level of feedback can be detrimental to the performance of a hearing implant, due to the sensitivity and fidelity of the signal input capabilities, the need for amplification of the signal, and the need for high fidelity signal output. Thus, even the smallest amounts of leakage, such as amounts that pass through a self-sealing membrane, can result in an unacceptable amount of feedback. On the other hand, different types of electronic medical implants (e.g., pacemakers, defibrillators, nerve stimulation devices) do not have such stringent sensitivity and fidelity requirements, and may be fully functional in the event of small amounts of leakage through a self-sealing membrane.

The invention claimed is:

1. A combination lead terminal and lead channel, the combination comprising:
   a lead terminal comprising a forward end, a distal end, a shaft between the forward end and the distal end, a terminal contact, and a gasket extending around an outer surface of the shaft on a distal side of the terminal contact,
   a lead channel comprising
      a channel wall,
      a channel contact,
      an open end, and
      a closed end distal to the channel contact, the closed end defined by surfaces that consist of a sidewall surface and a distal surface, wherein the sidewall surface and the distal surface are defined by a single continuous material surface, the lead channel adapted to receive the lead terminal, and
   an open vent extending through the channel wall from a channel vent hole fixed at a surface of the channel wall, to an exterior vent hole,
   wherein the lead terminal and lead channel are configured for the lead terminal to be inserted through the open end and into the channel and into a fully-inserted position wherein:

the terminal contact is electrically engaged with the channel contact, the gasket engages an inner surface of the channel wall to produce a seal, the gasket is located between the open end and the closed end, the channel vent hole is located between the gasket and the open end, and the terminal contact and channel contact are located between the gasket and the closed end.

2. A combination as recited at claim 1 wherein the lead terminal comprises a second terminal contact, the lead channel comprises a second channel contact, and, with the lead terminal inserted in the lead channel in the fully-inserted position the second terminal contact is electrically engaged with the second channel contact, wherein the second terminal contact and the second channel contact are located between the gasket and the closed end.

3. A combination as recited at claim 1 wherein the channel wall excludes a set screw capable of contacting the lead terminal to secure the lead terminal in the fully-inserted position.

4. A combination as recited at claim 1 wherein the vent excludes a self-sealing membrane.

5. A combination as recited at claim 1 wherein the open vent hole is a continuous open passage through the channel wall that allows fluid communication between the interior of the channel and an exterior location.

6. A combination as recited at claim 1 wherein the open vent hole is located a distance in a range from 0.25 to 10 millimeters from the gasket, with the lead terminal in the fully-inserted position.

7. A combination as recited at claim 1 wherein the open vent hole is located a distance in a range from 3 to 13 millimeters from the terminal contact, with the lead terminal in the fully-inserted position.

8. An electronic device comprising the combination of claim 1.

9. An electronic device as recited at claim 8 comprising a second combination lead terminal and lead channel, the second combination comprising:
a second lead terminal comprising a second forward end, a second distal end, a second shaft between the second forward end and the second distal end, a second terminal contact, and a second gasket extending about an outer surface of the second lead terminal on a distal side of the second terminal contact,
a second lead channel comprising
a second channel wall,
a second channel contact,
a second open end, and
a second closed end, the second lead channel adapted to receive the second lead terminal, and
a second open vent extending through the second channel wall from a second channel vent hole opening in the second channel, to a second exterior vent hole,
wherein the second lead terminal and second lead channel are configured for the second lead terminal to be inserted through the second open end and into the second channel and into a fully-inserted position wherein:
the second terminal contact is electrically engaged with the second channel contact,
the second gasket engages an inner surface of the second channel wall to produce a second seal,
the second gasket is located between the second open end and the second closed end the second channel vent hole is located between the second gasket and the second open end, and the second terminal contact and second channel contact are located between the second gasket and the second closed end.

10. A device as recited at claim 8 wherein the device is a hearing implant.

11. A device as recited at claim 10 comprising an electronic processor unit electrically connected to the channel contact, the electronic processor unit comprising an amplifier that amplifies an electronic signal received by the channel contact.

12. A device as recited at claim 1 wherein the lead terminal and lead channel are configured for the lead terminal to be inserted through the open end and into the channel and into a fully-inserted position wherein the vent hole in the channel is in fluid communication with the open end, with the lead terminal in the fully-inserted position.

13. A device as recited at claim 1 wherein the lead terminal and lead channel are configured for the lead terminal to be inserted through the open end and into the channel and into a fully-inserted position wherein the lead channel does not include any vent between the closed end and the gasket, with the lead terminal in the fully-inserted position.

14. A device as recited at claim 1 wherein the lead terminal and lead channel are configured for the lead terminal to be inserted through the open end and into the channel and into a fully-inserted position wherein no gasket is located between the vent and the open end, with the lead terminal in the fully-inserted position.

15. A device as recited at claim 1 wherein the vent is unobstructed.

16. A device as recited at claim 1 wherein the vent is located at a length-wise location of the channel that is between the open end and a location midway between the open end and the closed end.

17. A device as recited at claim 1 wherein the vent is located at a length-wise location of the channel that is between the open end and a distance from the open end that is ⅓ of the total length of the channel.

18. A device as recited at claim 1 wherein the vent is located at a length-wise location of the channel that is between the open end and a distance from the open end that is ¼ of the total length of the channel.

19. A combination of claim 1 wherein the open vent is a fixed and open channel extending through the channel wall between the channel vent hole and the exterior vent hole.

20. A method of assembling an electronic medical device, the method comprising:
providing a combination lead terminal and lead channel, the combination comprising:
a lead terminal comprising a forward end, a distal end, a shaft between the forward end and the distal end, a terminal contact, and a gasket extending around an outer surface of the shaft on a distal side of the terminal contact,
a lead channel comprising
a channel wall,
a channel contact,
an open end, and
a closed end, the lead channel adapted to receive the lead terminal, and
an open vent extending through the channel wall from a channel vent hole fixed at a surface of the channel wall, to an exterior vent hole, wherein the lead terminal and lead channel are configured for the lead terminal to be inserted through the open end and into the channel and into a fully-inserted position wherein:

the terminal contact is electrically engaged with the channel contact, the gasket engages an inner surface of the channel wall to produce a seal, the gasket is located between the open end and the closed end, the channel vent hole is located between the gasket and the open end, and the terminal contact and channel contact are located between the gasket and the closed end, inserting the lead terminal into the fully-inserted position, and implanting the device in a human patient with the vent open.

21. A method of claim 20 comprising: inserting the lead terminal into the fully-inserted position, while the vent is unobstructed.

22. A method of claim 21 wherein the exterior vent hole is a fixed opening located at a surface at an exterior of the channel wall.

* * * * *